(12) United States Patent
Yue et al.

(10) Patent No.: US 7,798,995 B2
(45) Date of Patent: Sep. 21, 2010

(54) ADJUSTABLE TIP NEEDLE APPARATUS

(75) Inventors: Andy Xin Yue, Toronto (CA); Raymond Georges Laborie, Toronto (CA); Vladislav Dudko, Concord (CA)

(73) Assignee: Laborie Medical Technologies, Inc., Mississauga, Ontario (CA)

( * ) Notice: Subject to any disclaimer, the term of this patent is extended or adjusted under 35 U.S.C. 154(b) by 0 days.

(21) Appl. No.: 12/249,624

(22) Filed: Oct. 10, 2008

(65) Prior Publication Data

US 2010/0094216 A1    Apr. 15, 2010

(51) Int. Cl.
*A61M 5/00* (2006.01)

(52) U.S. Cl. .......................... 604/117; 604/116
(58) Field of Classification Search ................. 604/117, 604/164.01–170.03, 116; 600/117
See application file for complete search history.

(56) References Cited

U.S. PATENT DOCUMENTS

| | | | |
|---|---|---|---|
| 4,932,936 A | 6/1990 | Dykstra et al. | |
| 5,261,889 A | 11/1993 | Laine et al. | |
| 5,674,205 A | 10/1997 | Pasricha et al. | |
| 5,935,141 A * | 8/1999 | Weldon | 606/167 |
| 6,004,295 A | 12/1999 | Langer et al. | |
| 6,071,230 A | 6/2000 | Henalla | |
| 6,083,222 A | 7/2000 | Klein et al. | |
| 6,162,917 A * | 12/2000 | Steffan et al. | 544/334 |
| 6,575,931 B1 | 6/2003 | Ponzi | |
| 6,589,232 B1 * | 7/2003 | Mueller | 606/15 |
| 6,939,322 B2 * | 9/2005 | Crank et al. | 604/117 |
| 2003/0093035 A1* | 5/2003 | Mohammed | 604/195 |
| 2004/0260327 A1 | 12/2004 | Mueller, Jr. et al. | |
| 2005/0187519 A1* | 8/2005 | Harris et al. | 604/117 |

* cited by examiner

*Primary Examiner*—Nicholas D Lucchesi
*Assistant Examiner*—Gerald Landry, II
(74) *Attorney, Agent, or Firm*—Cahn & Samuels, LLP

(57) ABSTRACT

The invention in at least one embodiment includes a device having a hub, a housing, a cannula, and a needle where the relative positions of the hub and the housing controls the relative positions of the cannula and the needle. In at least one embodiment, the housing includes a pathway in which a pin on the hub travels through to allow for selection of the insertion depth of the needle relative to the cannula.

21 Claims, 7 Drawing Sheets

ADJUSTABLE TIP NEEDLE APPARATUS

I. FIELD OF THE INVENTION

This invention relates to a device for controlling the insertion depth of a needle beyond the end of a cannula housing the needle, more particularly to a structure that maintains the depth of the needle relative to the cannula.

II. BACKGROUND OF THE INVENTION

Prior art systems use a needle that extends beyond the distal end of a cannula. The needle includes multiple markings along its length that extends beyond the cannula. The markings are counted after the needle is inserted. The number of markings is then translated into an insertion depth using a look-up table.

Other prior art needles and cannulas use markings at their tips that are detectable with X-rays and/or MRI systems to show the location of the tips with respect to the surrounding tissue.

III. SUMMARY OF THE INVENTION

In at least one embodiment according to the invention, the invention includes an apparatus having a hub having a handle, the hub having a passageway running lengthwise; a housing engaging the hub; a cannula extending from the housing on a surface of the housing spaced from the hub; a needle attached to the hub forming a fluid pathway from a distal end of the hub to a free end of the needle, the needle passing through the housing and coaxially located in the cannula; and a location of the hub relative to the housing controls a relative location of the needle to the cannula.

In at least one embodiment according to the invention, the invention includes an apparatus having a hub having a distal end, a proximal end, and a handle, the hub having a passageway from the distal end to the proximal end; a slider attached to the hub, the slider having a passageway running the length of the slider; a housing engaging the slider; a cannula extending from the housing on a surface of the housing spaced from the slider; a needle attached to the hub forming a fluid pathway from the distal end to a free end of the needle, the needle passing through the slider, the housing and the cannula; and a location of the slider relative to the housing controls a relative location of the needle to the cannula.

In at least one embodiment according to the invention, the invention includes an apparatus having a hub; a needle connected to the hub, the needle and the hub form a fluid pathway from a distal end of the apparatus to a proximal end of the apparatus; controlling means for controlling insertion depth of the needle; and a cannula connected to the controlling means and in sliding engagement of the needle.

A device in at least one embodiment includes an injection needle, a cannula, and a labyrinth mechanism. The device in at least one embodiment includes a housing, a movable component (or a slider) engaging the housing and a locking pin on the movable component. The device is configured for pushing out or retracting the movable component with respect to the housing. The injection needle is attached to the movable component while the cannula is attached to the housing. The injection needle passes through the cannula with the needle and the cannula being movable relatively to each other. The distance between the needle tip point and proximal end of the cannula is controlled and adjusted based on the position of the movable component relative to the housing, through placing the pin at different positions in the housing. When the device is used, a variable needle length is exposed out of the cannula. The device is designed to immobilize the movable component together with the needle at different positions in a path in the housing through a stop pin installed in the movable component. Subsequently, a desired penetration depth can be set for the needle tip. In at least one embodiment, the diameter of the cannula is much larger than that of the needle, the injection safety is assured especially for the thin wall organ injection.

Given the following enabling description of the drawings, the apparatus should become evident to a person of ordinary skill in the art.

IV. BRIEF DESCRIPTION OF THE DRAWINGS

The present invention is described with reference to the accompanying drawings. In the drawings, like reference numbers indicate identical or functionally similar elements. The use of cross-hatching and shading within the drawings is not intended as limiting the type of materials that may be used to manufacture the invention.

V. DETAILED DESCRIPTION OF THE DRAWINGS

Figure 1:
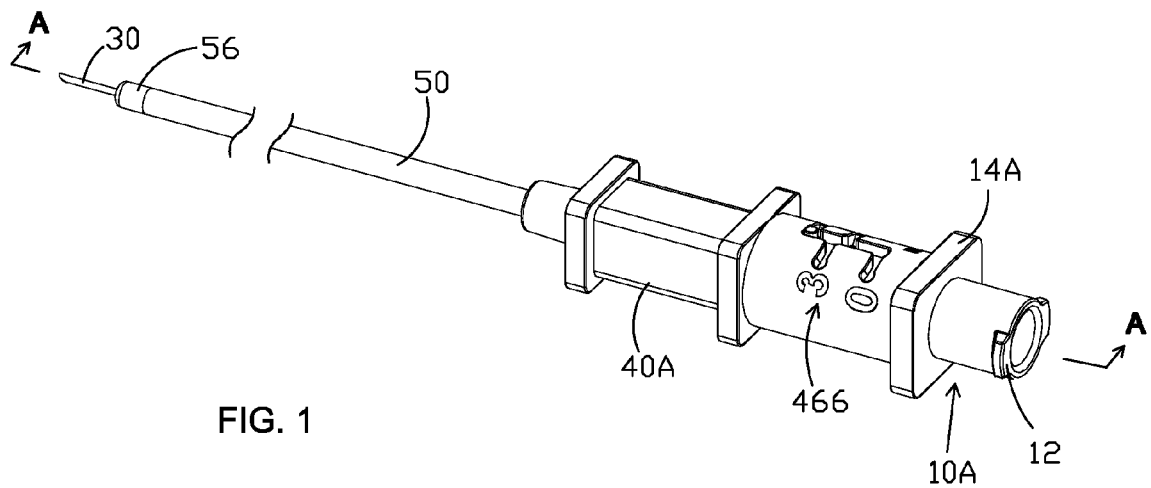
FIG. 1 illustrates a perspective view of an embodiment according to the invention.

The invention includes a device that allows the user to know the depth of insertion of the needle beyond the end of the cannula and to lock the relative positioning in place. The embodiments depicted in the figures illustrate different configurations according to the invention for controlling the insertion depth of a needle 30 beyond a cannula 50 using elements located at the distal end of the needle 30 and the cannula 50.

In the different embodiments, a hub 10 (and/or the slider 20) and a housing 40 are in rotational and sliding engagement with each other. In some embodiments, the engagement is limited by a pathway 46 present in the housing 40 and movement of a pin 29 in that pathway 46.

Figure 2:
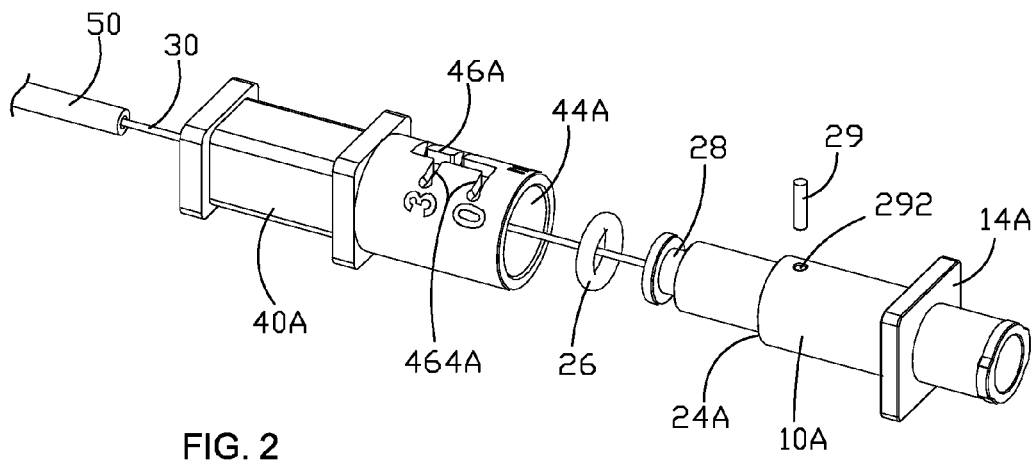
FIG. 2 illustrates a perspective exploded view of the embodiment illustrated in FIG. 1.
Figure 3:
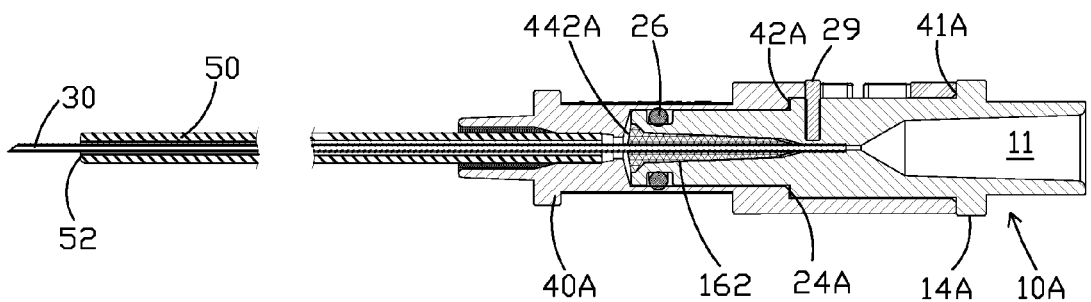
FIG. 3 illustrates a cross-sectional view of the embodiment illustrated in FIG. 1 taken along line A-A of FIG. 1.

FIGS. 1-3 illustrate an embodiment according to the invention. The illustrated embodiment includes a hub 10A attached to a needle 30. The hub 10A and the needle 30 are in sliding engagement with a housing 40A with the needle 30 passing through the housing 40A into a cannula (or sheath) 50. The needle 30 and the cannula 50 are coaxially located to each other. The housing 40A is attached to the cannula 50, and in an alternative embodiment these two components are integrally formed with the cannula 50 extending away from the housing 40A on an opposing surface of the housing 40A from where the hub 10A is located. The cannula 50, in at least one embodiment illustrated, for example, in FIG. 3, is embedded in a hole (or bore) in the proximal end of the housing 40A. Examples of ways to attach the cannula 50 to the housing 40A include, for example, insert molding, pressing-in molding, glue, adhesive, or bonding.

In at least one embodiment, the hub 10A includes a connecter 12, a handle 14A and a shoulder 24A. The hub 10A also includes a fluid receiving cavity 11 for transferring fluid from a dispensing device 90 into the needle 30. The fluid receiving cavity 11 extends in from the connector 12 and through the handle 14A to funnel fluid from a fluid delivery device into the needle 30. The illustrated connecter 12 is a male portion of a Luer-lock connection to facilitate connection to syringes and other fluid devices as illustrated, for example, in FIGS. 15 and 16; however, other connectors may be used instead of a Luer-lock connection.

Figure 5A:
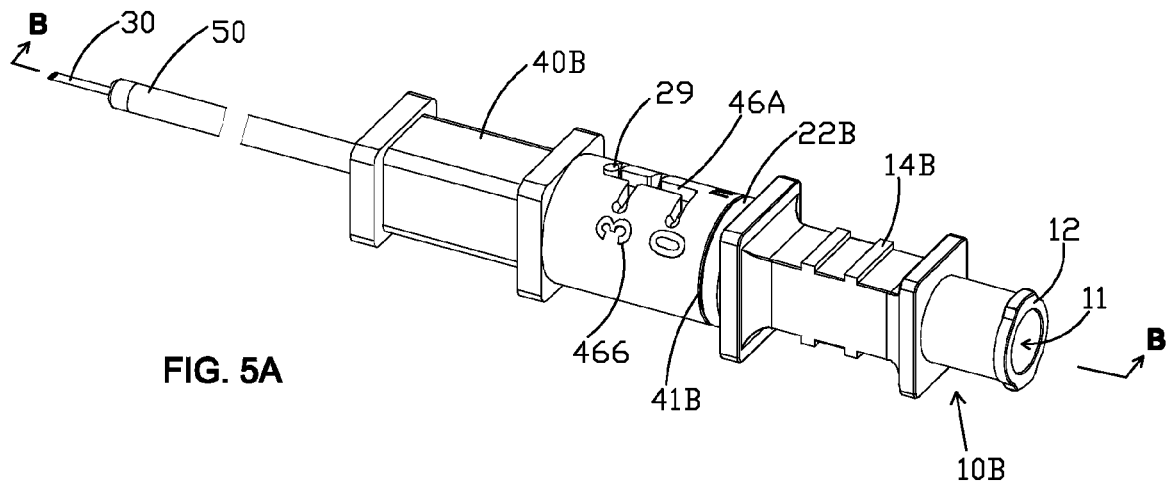
FIGS. 5A and 5B illustrate additional embodiments according to the invention with different handle configurations.

Although the hub 10A is illustrated as having a square cross-section for the handle 14A about the cavity 11, a variety of other cross-sections are possible for exterior of the handle 14A and likewise the housing 40A. Further, the handle 14A in at least one embodiment is lengthened to include ridges (as illustrated, for example, in FIGS. 5A and 5B) although other gripping structures or surfaces could be used in place of the illustrated ridges.

The hub 10A further includes a second cavity 162 extending from its proximal end towards the fluid receiving cavity 11, and with in at least one embodiment a short passageway connects the cavities. The cavities 11, 162 and any interconnection between these cavities from a passageway (or bore) passing through the hub 10A. In at least one embodiment the needle 30 passes through the second cavity 162 to establish a fluid connection with the first cavity 11, although a variety of attachment points can be used to establish a fluid path from the distal end of the hub 10A into the needle 30. In at least one embodiment as illustrated in FIG. 3, material is filled into the second cavity 162 around the needle 30 to secure the needle 30 in place in the hub 10A. Examples of material include, but are not limited to, glue, adhesive, or other bonding material including necessary hardeners. Another example of how to attach the needle 30 to hub 10A is to use insert molding.

In at least one embodiment, the handle 14A acts as a safety barrier and restricts the depth of insertion of the needle 30 relative to the cannula 50 when the handle 14A abuts against the distal end 41A of the housing 40A. The distal end 41A may include a flange or other increased surface area to abut against the handle 14A. The illustrated embodiment in FIG. 3 also shows an alternative safety stop where the hub 10A has a shoulder 24A that will abut against the shoulder 42A in the housing 40A when the maximum insertion difference between the needle 30 and the cannula 50 has been reached. These two embodiments could be used individually or together.

The housing 40A includes a cavity 44A for receiving a portion of the hub 10A. In the illustrated embodiment, a rubber O-ring 26 is located between the hub 10A and the wall of the cavity 44A of the housing 40A, in part, to provide a surer fit between these components. In at least one embodiment, the presence of the O-ring 26 reduces or even prevents possible back fluid flow out of the housing 40A, for example, of body fluid from a patient. In at least one embodiment, the O-ring 26 reduces or prevents air leakage from the patient's bladder during a procedure. In at least one embodiment, the O-ring 26 provides frictional resistance to the hub 10A moving to prevent the hub 10A together with the needle 30 from moving accidentally or too easily in use. The O-ring 26 is illustrated in FIGS. 2 and 3 and it resides in an annular channel 28 near the proximal end of the hub 10A. In an alternative embodiment (not illustrated), the O-ring 26 and the corresponding channel 28 are omitted from the hub 10A.

The hub 10A and the housing 40A together control the level of insertion of the needle 30 beyond the proximal (or free) end 52 of the cannula 50 along with providing an indication of the level of needle insertion during use. For example, the illustrated embodiment of FIGS. 2 and 4A-4D is an example of this interface. The hub 10A includes a guide/lock pin 29 extending axially away from the hub 10A. As illustrated in FIGS. 2 and 3, the pin 29 may be inserted and affixed in a hole 292 in the hub 10A during, for example, manufacture. The housing 40A includes a pathway 46A through which the pin 29 travels. The illustrated pathway 46A includes a main slot 462A running in the direction of the needle 30 with a plurality of slots 464A in communication with and extending from the main slot 462A. In at least one embodiment, the plurality of slots 464A are perpendicular to the main slot 462A. The illustrated pathway 46A includes millimeter markings 466 (indicia for indicating insertion depth of the needle or means for providing level of needle insertion) of 0, 2, 3, and 5 to indicate the distance the needle 30 extends beyond the cannula 50. In at least one embodiment, when the pin 29 is in the slot labeled 0, the end of the needle is retracted into the cannula 50 by a predetermined distance with examples being 0-2 mm with a particular example being 1 mm although other distances are possible. In at least one embodiment, the needle 30 extends at least 5 mm beyond the cannula 50 for its deepest insertion depth. Although the illustration includes a millimeter example, one of ordinary skill in the art will appreciate that other distances may be used than those illustrated along with using different measurement units such as inches. The illustrated pathway 46A alternates the secondary (or locking) slots 464A from side to side to improve the level of insertion control other what would be possible if all of the slots 464A were on the same side of the main slot 462A. As discussed later, there are a variety of ways in which depth control of the needle 30 beyond the catheter 50 can be accomplished as part of the invention.

In at least one embodiment, the locking slots 464 include a lateral section 4642A that has a width approximately that of the pin 29 or in some embodiments slightly smaller than the pin to provide resistance to passage of the pin 29. At the free end of the locking slot 464, there is a hole (or opening) 4644A sized to fit the pin 29 into and hold the pin in place unless a force is applied to move the pin 29 back through the respective lateral section 4642A. The pin 29 is held in place in this embodiment because it will resist moving back through the lateral section of the slot because the lateral section is sized to match the pin 29 diameter or be slightly smaller. For example, FIGS. 4A-4E illustrate this configuration of the locking slot; and although a crescent shape is illustrated for the hole 4644A, other shapes are possible to hold the pin 29 in place. In some embodiments, when the pin 29 reaches the opening 4644A there is a clicking sound as the pin 29 moves into place.

FIG. 3 also illustrates an example of a gap 442A existing between the proximal end of the hub 10A and the distal end of the housing cavity 44A when the hub 10A is fully inserted into the housing 40A. The gap 442A provides a separation space between the housing 40A and the proximal end of the hub 10A allows for imperfections in the flat surface from the adhesive used to attach the needle 30 to the hub 10A. In at least one embodiment, the strength of the bonding characteristics of the adhesive between the needle 30 and the hub 10A is above 30 pounds.

Figure 5B:
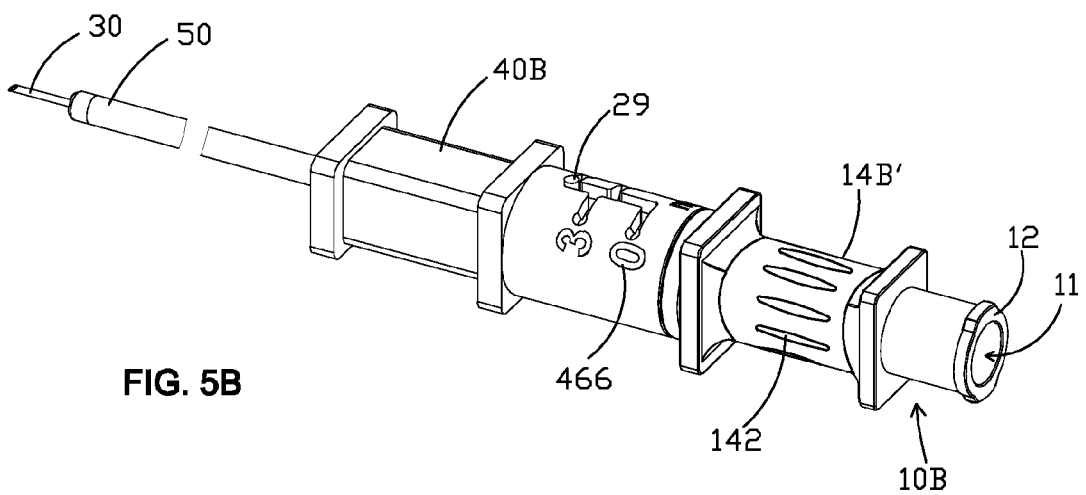
Figure 6:
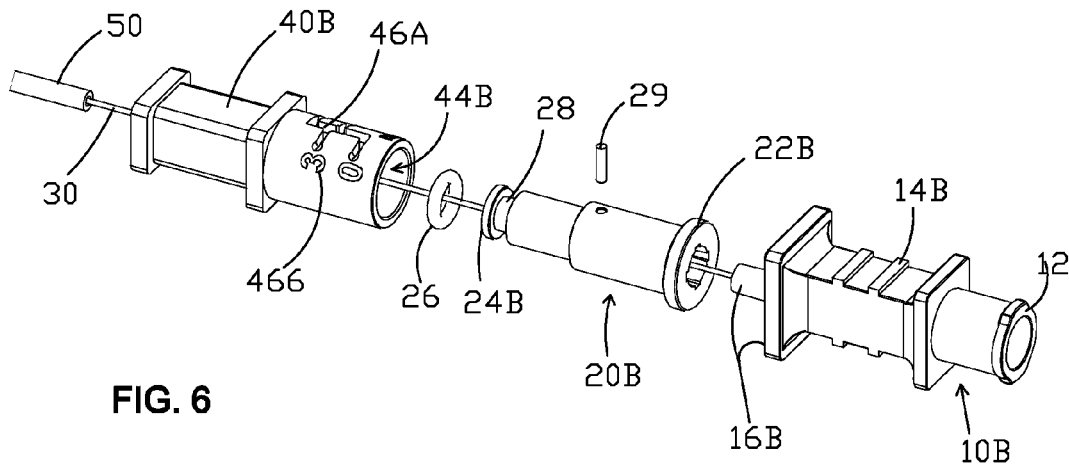
FIG. 6 illustrates a perspective exploded view of the embodiment illustrated in FIG. 5A.
Figure 7:
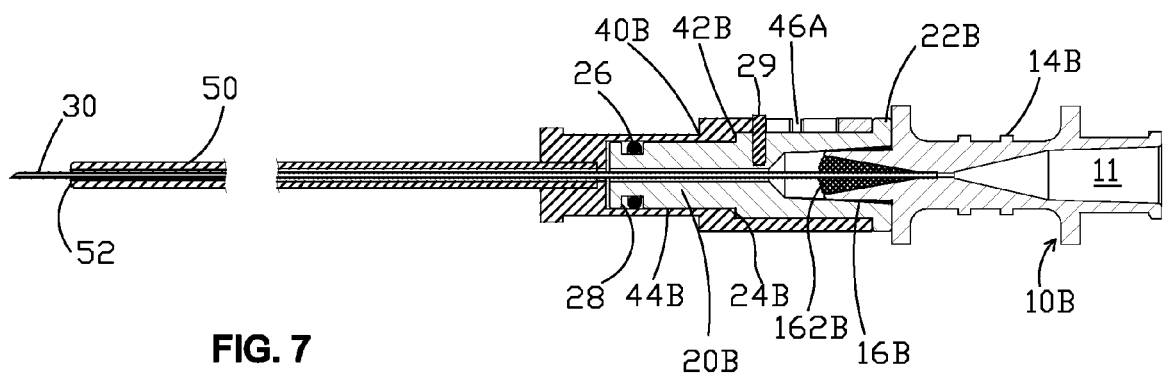
FIG. 7 illustrates a cross-sectional view of the embodiment illustrated in FIG. 5A taken along the line B-B of FIG. 5A.

FIGS. 5A-7 illustrate additional embodiments according to the invention. The illustrated embodiment includes a hub 10B attached to a slider 20B and a needle 30. In an alternative embodiment, the hub 10B and the slider 20B are formed as an integral piece, for example, as discussed previously in connection with FIGS. 1-4D where the combined pieces were the hub 10A. The slider 20B and the needle 30 are in sliding engagement with a housing 40B with the needle 30 passing through the housing 40B into a cannula 50. The housing 40B is attached to the cannula 50, and in an alternative embodiment these two components are integrally formed with the cannula 50 extending away from the housing 40B on an opposing surface of the housing 40B from where the hub 10B is located. The cannula 50, in at least one embodiment illustrated, for example, in FIG. 7, is embedded in a hole in the proximal end of the housing 40B. Examples of ways to attach these components include, for example, insert molding, pressing-in molding, glue, adhesive, or bonding.

In at least one embodiment, the hub 10B includes a connecter 12, a handle 14B and a slider interface 16B. The connecter 12 includes a fluid receiving cavity 11 for transferring fluid from a dispensing device 90 into the needle 30. The fluid receiving cavity 11 extends into the handle 14B to funnel fluid from a fluid delivery device into the needle 30.

Although the hub 10B is illustrated as having a square cross-section for the handle 14B about the cavity 11 and needle 30, a variety of other cross-sections are possible for the handle 14B. Further, the handle 14 in at least one embodiment includes ridges (as illustrated, for example, in FIGS. 5A and 6) although other gripping structures or surfaces could be used in place of the illustrated ridges. FIG. 5B illustrates an alternative handle 14B' which includes a plurality of protrusions 142 running parallel with the needle 30. Although a square cross-section is utilize for sections of the hub and the housing, these shapes likewise may be replaced with other cross-sections that would facilitate gripping by fingers or other manipulative objects such as robotic members.

The slider interface 16B extends from the handle 14B and includes a cylindrical wall that provides a surface to engage the slider 20B and in some embodiments the cylindrical wall is joined with adhesive or other approaches to the interior of the slider 20B. The second cavity 162B on the inside of the cylindrical wall is in communication with the first cavity 11. In at least one embodiment the needle 30 passes through the second cavity 162B and is connected to the first cavity 11 located inside of the handle 14B, although a variety of attachment points can be used to establish a fluid path from the distal end of the hub 10B into the needle 30. In at least one embodiment as illustrated in FIG. 7, material is filled into the second cavity 162 around the needle 30 to secure the needle 30 in place in the hub 10B. Examples of material include, but are not limited to, glue, adhesive, or other bonding material including necessary hardeners. Another example of how to attach the needle 30 to hub 10B is to use insert molding.

In the embodiment illustrated in FIGS. 5-7, the slider 20B includes a flange 22B at its distal end for abutting against the hub 10B. In at least one embodiment the flange 22B is used to increase the surface area for placing adhesive onto to strengthen the connection between the slider 20B and the hub 10B. The flange 22B in at least one embodiment acts as a safety barrier and restricts the depth of insertion of the needle 30 relative to the cannula 50 when the flange 22B abuts against the distal end 41B of the housing 40B. The illustrated embodiment, the slider 20B includes a shoulder 24B that will abut against the shoulder 42B within the housing 40B when the maximum insertion difference between the needle 30 and the cannula 50 has been reached.

The housing 40B includes a cavity 44B in which the slider 20B resides. In the illustrated embodiment, a rubber O-ring 26 is located between the slider 20B and the wall of the cavity 44B of the housing 40B, in part, to provide a surer fit between these components. In at least one embodiment, the presence of the O-ring 26 reduces or even prevents possible back fluid flow out of the housing 40B. In at least one embodiment, the O-ring 26 provides frictional resistance to the slider 20B moving to prevent the slider 20B together with the needle 30 from moving accidentally or too easily in use. The O-ring 26 is illustrated in FIGS. 6 and 7 and it resides in an annular channel 28 near the proximal end of the slider 20B. In at least one embodiment, the housing cavity 44B expands radially out to form an annular shoulder 42B that acts as a further block to movement of the slider 20B as illustrated, for example, in FIG. 3. In an alternative embodiment, the O-ring 26 and the corresponding channel 28 are omitted from the slider 20B.

The slider 20B and the housing 40B control the level of insertion of the needle 30 beyond the proximal (or free) end 52 of the cannula 50 along with providing an indication of the level of insertion. For example, the illustrated embodiment of FIGS. 4A-4D is an example of this interface. The slider 20B includes a guide/lock pin 29 extending axially away from the slider 20B. The housing 40B includes a pathway 46A through which the pin 29 travels.

Figure 8:
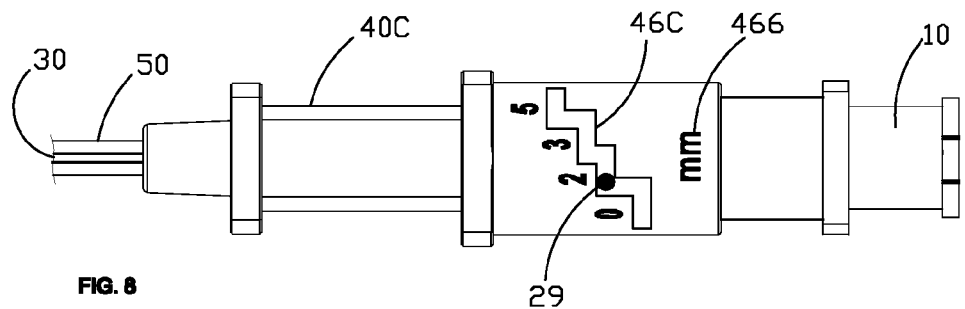
FIGS. 8 and 9 illustrate different insertion control embodiments according to the invention.

An alternative pathway 46C in the housing 40C is illustrated in FIG. 8 where there is a plurality of segments connected at 90 degree angles forming a stairway patterned slot. Each level of the stairway pattern represents a different insertion depth of the needle 30. In at least one embodiment, each level is accompanied by a measurement (or other marking) 466 representing the depth of insertion of the needle 30 relative to the cannula 50. In an alternative embodiment, a torsion spring is wrapped around the hub 10 (or the slider 20 depending upon the embodiment) to push the pin 29 against the left side of the respective segment, which are running perpendicular to the needle 30, where the pin 29 is located.

Figure 9:
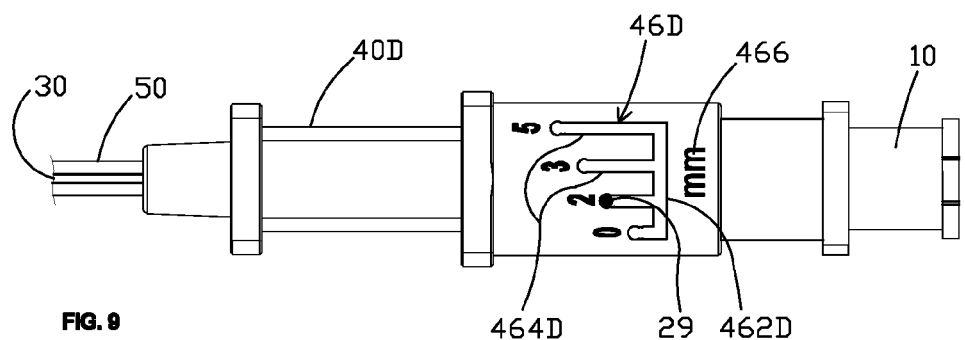

A further embodiment is illustrated in FIG. 9 and includes a hub 10 with a pin 29 to allow the hub 10 to move relative to the housing 40D with the pathway 46D. The housing 40D includes a series of axially cut slots 464D running parallel to the needle 30 connected by a lateral slot 462D for engagement by pin 29. In the illustrated embodiment, the housing 40D includes a marking 466 near to each axial slot to indicate the relative insertion depth of the needle 30 beyond the proximal tip 52 of the cannula 50. In at least one embodiment, a spring is mounted on the hub 10 and held in place between pin 29 and the distal end of the housing 40D as illustrated in FIG. 9.

Figure 10:
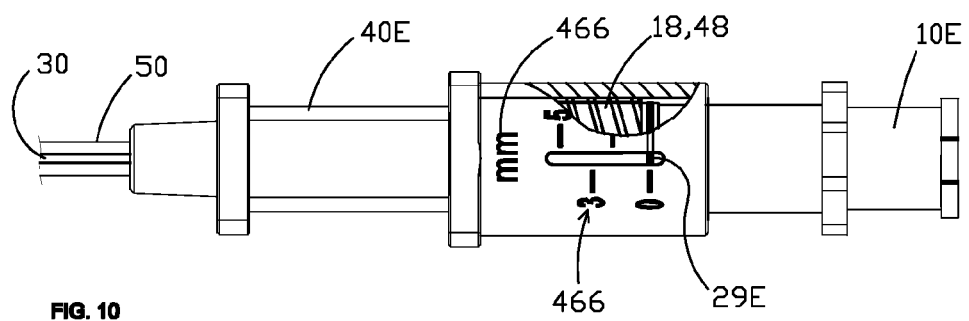
FIGS. 10 and 11 illustrate different insertion control embodiments according to the invention with each figure including a partial cross-sectional view.

A further embodiment is illustrated in FIG. 10, which illustrates a hub 10E having a threaded section 18 for engagement with a corresponding threaded section 48 of housing 40E. As the hub 10E is rotated it moves relative to the housing 40E and causes the tip of the needle 30 to move relative to the end 52 of the cannula 50. In at least one embodiment, the housing 40E is clear and the hub 10E includes a marking 29E such as a dot or line (or alternatively a portion of the hub includes a contrasting color from the distal end to the location of the marking) that is matched to measurement indicia located on the housing 40E. In an alternative embodiment, the hub 10E includes a plurality of markings 466 along its length that are covered up as it is inserted into the housing 40E such that the smallest measurement is next to the housing 40E with the largest measurement closest to the hub 10E.

Figure 11:
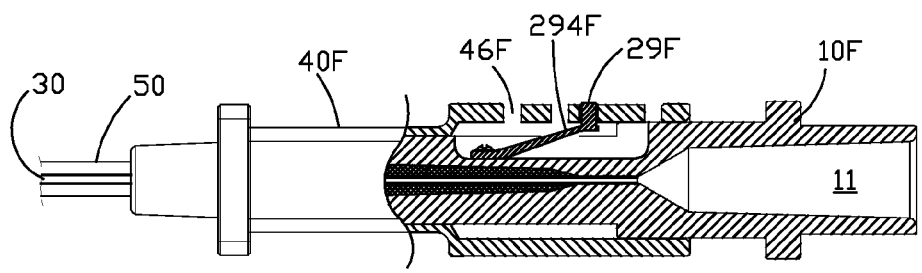

A still further embodiment is illustrated in FIG. 11, which shows a housing 40F with a series of holes 46F running parallel to the needle 30 along its outer surface. The illustrated embodiment includes a hub 10F having a pin (or button) 29F that is depressed below the top surface of the housing 40F to allow the slider 20F to move relative to the housing 40F before the pin 29F engages the next hole along the top surface of the housing 40F. The pin 29F in at least one embodiment resides on a lever spring 294F that urges the pin 29F through an available hole 46F. In an alternative embodiment, the slider 20F includes a visual indicator visible through the housing 40F to indicate where the pin is relative to the holes to allow for determination of the insertion depth of the needle 30 relative to the cannula 50. The previously described shoulders 24, 42 are examples of elements that would restrict the insertion depth of the needle. At the distal end of the housing 40, an inner extending flange could act as a stop for the pin 29F. The inner flange in at least one embodiment assists with centering the hub/slider in the housing. In at least one embodiment, the flange would be lined with a gasket to engage the hub/slider.

The variety of combinations of hubs and/or sliders with housings having different pathways and depth control features described above collectively can be called means for controlling insertion depth of a needle.

Figure 4A:
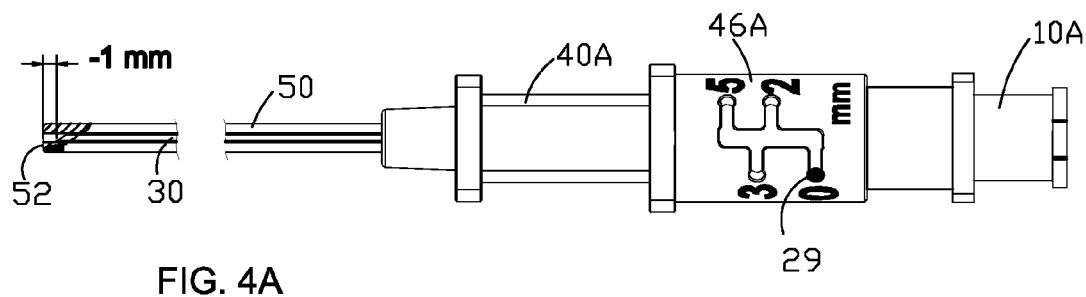
FIGS. 4A-4D illustrate the placement of a pin in different slots in an example of a configuration according to the invention. In each figure, the distance between the needle tip and the cannula tip is shown in millimeters as discussed in connection with the illustrated embodiments.
Figure 4B:
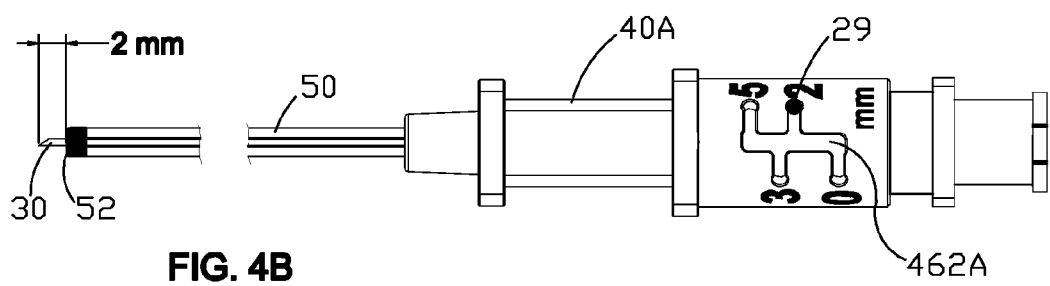
Figure 4C:
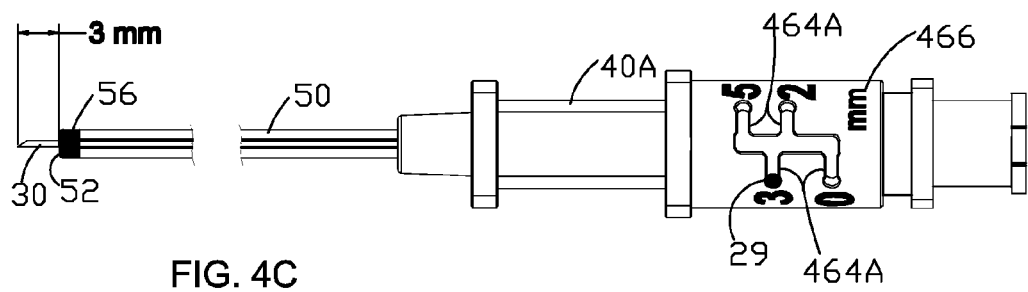
Figure 4D:
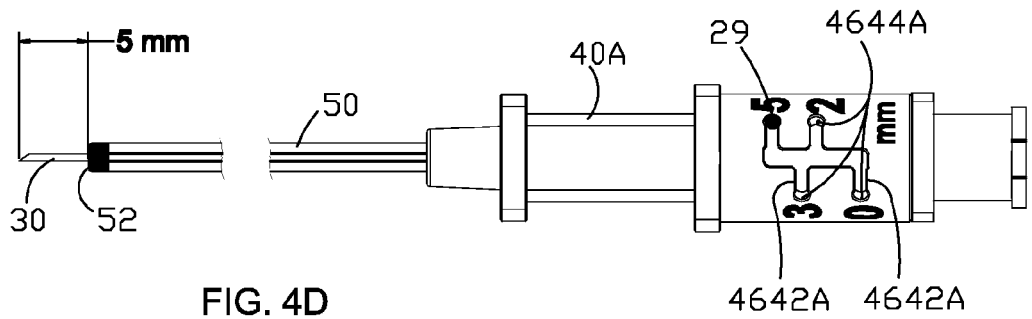
Figure 12:
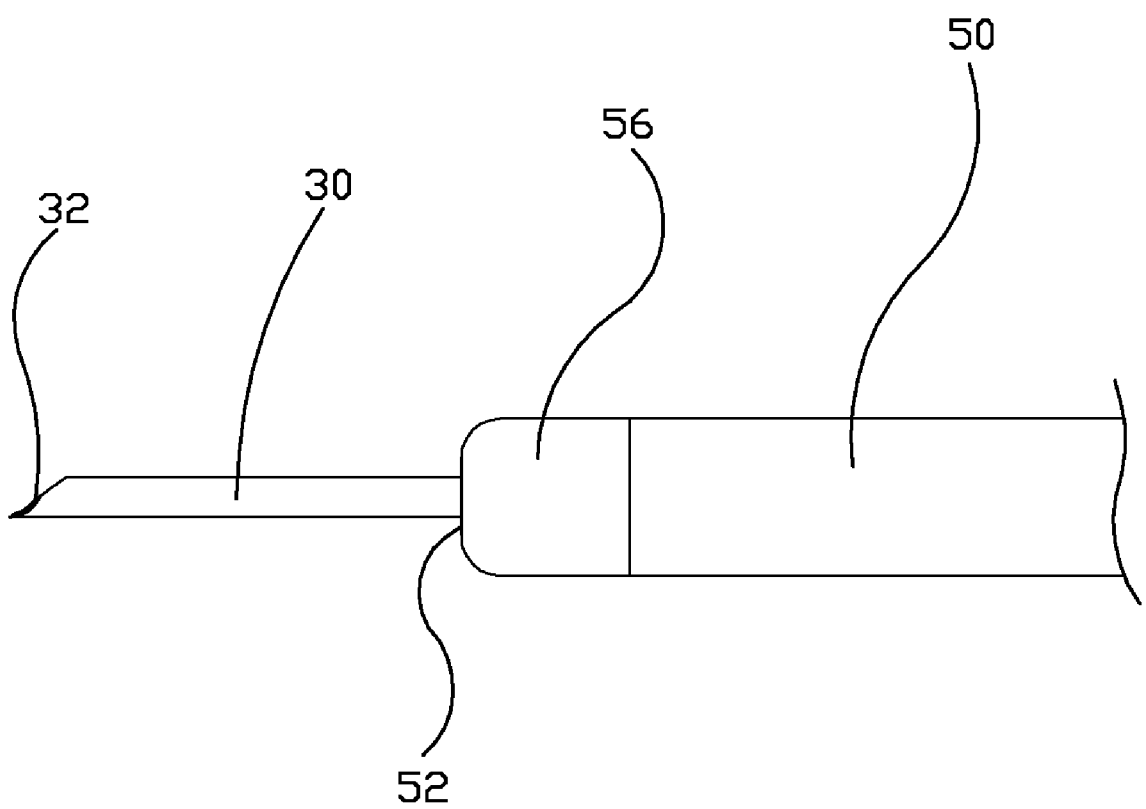
FIG. 12 illustrates an enlarged view of the ends of a cannula and a needle of another embodiment according to the invention.

FIG. 12 illustrates an embodiment of the invention where the cannula 50 includes a contrasting color band (or needle tip indicator) 56 near the proximal tip 52. For example, FIGS. 1 and 4C provide additional examples of the contrast band 56. For example, if the cannula is a light blue color, then the contrasting color band could be black. The presence of the contrasting (color) band 56 provides ready identification of the cannula proximal tip 52 relative to the needle tip 32 with a cystoscope light during use. In an alternative embodiment, the cannula tip 52 expands (or flares) out from the rest of the cannula 50 to increase the surface area that will contact the patient's tissue.

In at least one embodiment, the cannula 50 and the needle 30 are made from flexible material to allow use with, for example, a flexible cystoscope. While in other embodiments, one or both of the cannula 50 and the needle 30 may be semi-rigid for use with, for example, a rigid cystoscope.

Examples of lengths for the cannula 50 include 30 cm to 65 cm, more particularly 35 cm to 50 cm. Further examples are 35 cm, 45 cm, and 50 cm. The needle 30 will typically be longer than the cannula 50 in an amount of the maximum desired insertion length plus the distance to connect with the hub/slider. When pin 29 is positioned at the 0 mm mark in the illustrated embodiments, the needle 30 in at least one embodiment is in a retracted state within the cannula 50, for example, the tip of the needle 30 is inside of the cannula 50 by 1 mm. The needle 30 is sized to slide within the cannula 50, for example, if the cannula 50 has an outer gauge of 5-7 FR with an inner size of 0.5-1.0 mm, then a needle 30 with a gauge of 22 g-27 g will be able to passthrough the cannula 50.

Although the various illustrated embodiments use circular cross-sections for the various channels internal to the device, different shapes may be utilized instead although it is preferred to have the needle and cannula have a circular cross-section.

Figure 13:
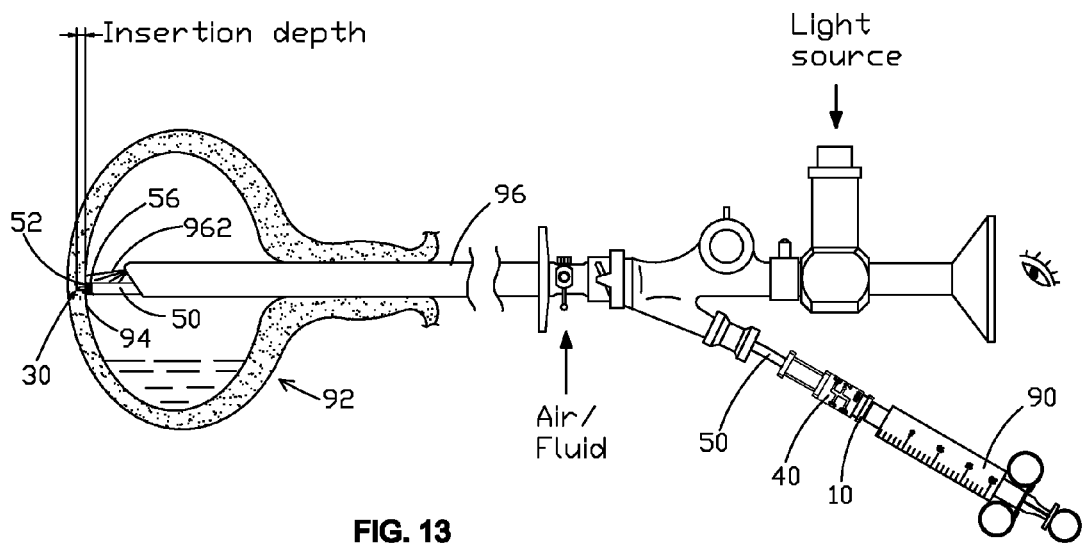
FIG. 13 illustrates a use of an embodiment according to the invention with a syringe and a rigid cystoscope.
Figure 14:
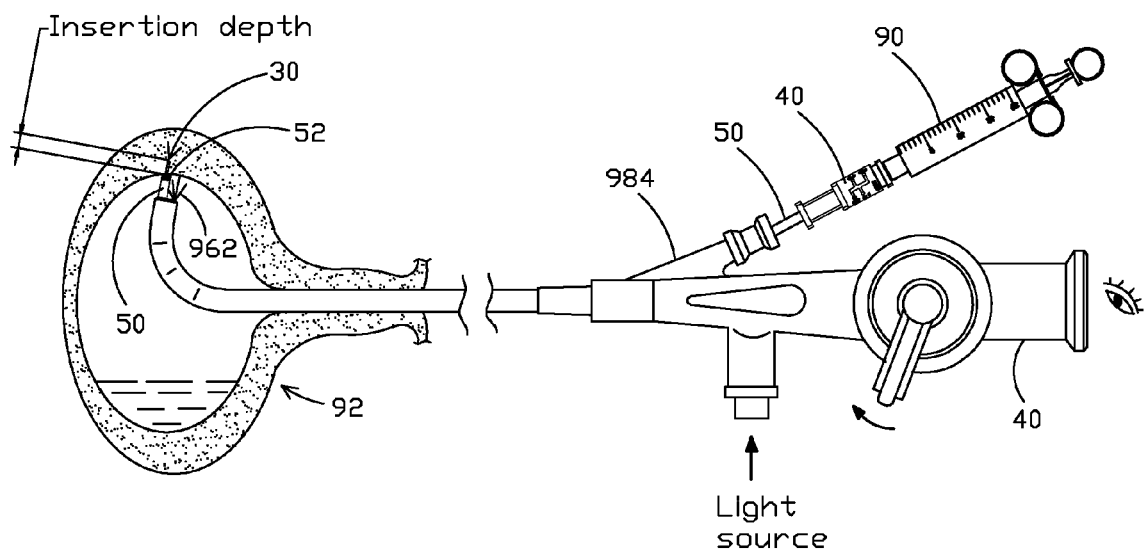
FIG. 14 illustrates a use of an embodiment according to the invention with a syringe and a flexible cystoscope.

FIGS. 13 and 14 illustrate an embodiment of the invention in use. FIG. 13 illustrates the device being inserted into a patient with the end 52 of the cannula 50 abutting against the tissue wall 92 of the injection site 94 with the needle 30 inserted into the tissue wall 92. Also shown in the FIG. 13 in phantom is a rigid cystoscope 96 (although other delivery devices could be used such as an endoscope) shining a light 962 onto the injection site 94. The cannula 50 is inserted into and through the cystoscope 96. At the distal end of the device the syringe 90 is connected to the hub 10 to allow injection of the contents of the syringe 90 into the tissue at the injection site 94.

FIG. 14 illustrates an embodiment of the invention being inserted into a flexible cystoscope 98. The cystoscope 98 includes a working channel 984 that runs along the main instrument. The cannula 50 of the illustrated embodiment is inserted in and through the working channel 984 to abut against the tissue region 92 of interest. As discussed above in connection with an alternative embodiment, the cannula 50 may include a cap 54 at its proximal end to allow for a larger surface area to be used to abut against tissue 92 and to decrease the likelihood of an inadvertent penetration into the tissue except for the needle 30. As illustrated in FIG. 14, the cystoscope 98 is proximate to the tissue region 92 to allow for the user to view the region of interest. Attached to the distal end of the hub 10 is a syringe 90 for injecting a desired fluid into the tissue region 92. The illustrated housing shows that the needle 30 is inserted 3 millimeters beyond the cannula 50 into the tissue at the injection site 94.

The invention also includes a method of use of the device. For example, a cystoscope (or endoscope) is inserted into the urinary tract of the patient until the proximal end is close to the target tissue. A syringe or other fluid dispensing device filled with medical solution is attached to the hub 10 and then the device is primed to remove any air bubbles from the device and the syringe. The pin 29 is set to its home position "0" (if not already there). The cannula 50 is inserted into the working channel of cystoscope such that the cannula 50 and the needle 30 extend beyond the cystoscope until the contrast band 56 can be clearly visible under a light 962.

After the device is positioned in the cystoscope, the injection steps begin. The needle insertion depth is set depending on the tissue wall thickness of the injection site 94. The tissue of the desired injection site 94 is punctured with the needle 30 by moving either the cystoscope (for example, if a rigid cystoscope is being used) and/or the needle 30 and cannula 50 (for example, if a flexible cystoscope is being used) towards the injection site 94. When the injection site 94 is punctured, then the fluid is dispensed from the syringe 90 through the device and out the needle 30 into the targeted tissue of the patient. Typically, the injection steps are repeated at 20 to 30 injection sites with adjustment of the pin 29 occurring between different injections to change the insertion depth of the needle 30 to reflect different tissue thicknesses in the patient.

After the injection procedure is complete, the pin 29 is adjusted to home position "0" to retract the tip of the needle 30 back inside the cannula 50. Then, the device is removed from the cystoscope followed by removal of the cystoscope from the patient. One of ordinary skill in the art will appreciate based on this disclosure that these steps can be rearranged and/or reordered within the scope of the above-described method.

The exemplary and alternative embodiments described above may be combined in a variety of ways with each other. Furthermore, the steps and number of the various steps illustrated in the figures may be adjusted from that shown.

It should be noted that the present invention may, however, be embodied in many different forms and should not be construed as limited to the embodiments set forth herein; rather, the embodiments set forth herein are provided so that the disclosure will be thorough and complete, and will fully convey the scope of the invention to those skilled in the art. The accompanying drawings illustrate exemplary embodiments of the invention.

Although the present invention has been described in terms of particular exemplary and alternative embodiments, it is not limited to those embodiments. Alternative embodiments, examples, and modifications which would still be encompassed by the invention may be made by those skilled in the art, particularly in light of the foregoing teachings.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

We claim:

1. An apparatus comprising:
a hub having a handle and a pin, said hub having a passageway running lengthwise;
a housing engaging said hub, said housing including a pathway having at least three connected slots through which said pin travels;
a cannula extending from said housing on a surface of said housing spaced from said hub;
a needle attached to said hub forming a fluid pathway from a distal end of said hub to a free end of said needle, said needle passing through said housing and coaxially located in said cannula; and
a location of said hub relative to said housing controls a relative location of said needle to said cannula.

2. An apparatus comprising:
a hub having a pin and a passageway running lengthwise;
a housing engaging said hub, said housing includes a pathway having
a main slot and
a plurality of secondary slots extending away from said main slot;
a cannula extending from said housing on a surface of said housing spaced from said hub;
a needle attached to said hub forming a fluid pathway from a distal end of said hub to a free end of said needle, said needle passing through said housing and coaxially located in said cannula; and
a location of said hub relative to said housing controls a relative location of said needle to said cannula, and
said pin engages said pathway.

3. The apparatus according to claim 2, wherein said housing includes indicia representative of insertion depth of said needle, said indicia proximate to respective secondary slots.

4. The apparatus according to claim 2, wherein said secondary slots include a first slot located at the distal end of the main slot, at least one slot located at a point spaced from the ends of the main slot, and a third slot located at the proximal end of the main slot.

5. The apparatus according to claim 4, wherein when said pin is in the first slot, the needle free end is positioned inside of said cannula, and
when said pin is in the third slot, the needle free end is positioned at farthest point from the end of said cannula.

6. The apparatus according to claim 5, wherein the farthest point is greater than or equal to 5 mm.

7. The apparatus according to claim 1, wherein said needle and said cannula are flexible.

8. The apparatus according to claim 1, wherein said cannula includes a contrast band near its free end.

9. The apparatus according to claim 1, wherein the at least three connected slots are connected in series with each connected to at least one adjacent slot at a substantially right angle.

10. An apparatus comprising:
a hub having a distal end, a proximal end, and a handle, said hub having a passageway from said distal end to said proximal end;
a slider fixedly and directly attached to said hub, said slider having a passageway running the length of said slider;
a housing engaging said slider;
a cannula extending from said housing on a surface of said housing spaced from said slider;
a needle attached to said hub forming a fluid pathway from said distal end to a free end of said needle, said needle passing through said slider, said housing and said cannula; and
a location of said slider relative to said housing controls a relative location of said needle to said cannula.

11. The apparatus according to claim 10, wherein said housing includes a pathway having a main slot and a plurality of secondary slots extending away from said main slot, and
said slider includes a pin for engaging said pathway.

12. The apparatus according to claim 11, wherein said housing includes indicia representative of insertion depth of said needle, said indicia proximate to respective secondary slots.

13. The apparatus according to claim 10, wherein said slider includes
a annular channel near its proximal end, and
a ring located in the annular channel.

14. The apparatus according to claim 1, wherein the pathway having at least three connected slots includes a main slot and a plurality of secondary slots extending and connected to the main slot, and
said housing includes for each secondary slot an opening at the end of the secondary slot spaced from said main slot.

15. The apparatus according to claim 1, wherein said hub includes
an annular channel near its proximal end, and
a ring located in the annular channel and contacting an interior of said housing.

16. The apparatus according to claim 15, wherein said ring is compressed between said housing and said annular channel.

17. The apparatus according to claim 2, wherein said housing includes for each secondary slot an opening at the end of the secondary slot spaced from said main slot where said opening has a diameter approximating the diameter of said pin.

18. The apparatus according to claim 17, wherein a width of each secondary slot measured in a direction parallel to the lengthwise direction of the main slot is smaller than a width of the main slot measured in a direction perpendicular to said needle.

19. The apparatus according to claim 2, wherein each of the secondary slots is connected at right angles to the main slot.

20. The apparatus according to claim 2, wherein a width of each secondary slot measured in a direction parallel to the lengthwise direction of the main slot is smaller than the diameter of said pin.

21. The apparatus according to claim 2, wherein a width of the main slot measured in a direction perpendicular to said needle is at least as large as the diameter of said pin.

\* \* \* \* \*